(12) United States Patent
Kawauchi et al.

(10) Patent No.: US 8,101,674 B2
(45) Date of Patent: Jan. 24, 2012

(54) RUBBER COMPOUND AND MOLDED ARTICLE

(75) Inventors: Yasushi Kawauchi, Tokyo (JP); Katsuhiko Kimura, Osaka (JP)

(73) Assignee: Daikyo Seiko, Ltd., Tokyo (JP)

( * ) Notice: Subject to any disclaimer, the term of this patent is extended or adjusted under 35 U.S.C. 154(b) by 0 days.

(21) Appl. No.: 12/668,377

(22) PCT Filed: Jun. 9, 2008

(86) PCT No.: PCT/JP2008/060528
§ 371 (c)(1), (2), (4) Date: Jan. 8, 2010

(87) PCT Pub. No.: WO2009/013945
PCT Pub. Date: Jan. 29, 2009

(65) Prior Publication Data
US 2010/0197862 A1    Aug. 5, 2010

(30) Foreign Application Priority Data
Jul. 25, 2007   (JP) .................................. 2007-192930

(51) Int. Cl.
C08F 2/46 (2006.01)
C08L 9/00 (2006.01)
C08L 7/00 (2006.01)

(52) U.S. Cl. ............ 522/157; 525/232; 525/88; 525/89; 525/157; 525/158; 525/159; 526/348.6; 264/494; 264/496; 524/230; 524/528; 524/261; 522/150; 522/155; 522/153

(58) Field of Classification Search .................... 525/88, 525/89, 232, 157, 158, 159; 526/348.7; 522/150, 522/155, 153; 524/230, 528, 261; 264/494, 264/496
See application file for complete search history.

(56) References Cited

U.S. PATENT DOCUMENTS

| | | | |
|---|---|---|---|
| 2003/0100696 A1* | 5/2003 | Muraki | 526/348.7 |
| 2005/0027062 A1* | 2/2005 | Waddell et al. | 524/496 |
| 2006/0004144 A1* | 1/2006 | Kimura et al. | 525/198 |
| 2006/0189755 A1* | 8/2006 | Chino et al. | 525/88 |

FOREIGN PATENT DOCUMENTS

| | | |
|---|---|---|
| EP | 2006328 | * 12/2008 |
| JP | 3-152164 | 6/1991 |
| JP | 5-043743 | 2/1993 |
| JP | 5-212104 | 8/1993 |
| JP | 5-269201 | 10/1993 |
| JP | 6-098921 | 4/1994 |
| JP | 6-269201 | 9/1994 |
| JP | 7-304909 | 11/1995 |
| JP | 2004-161816 A | 6/2004 |
| JP | 2004-204181 A | 7/2004 |
| JP | 2005068224 | 3/2005 |
| JP | 2007054621 | 3/2007 |
| JP | 2007119528 | 5/2007 |
| WO | WO2006/098142 | 9/2006 |
| WO | WO2007/119687 | 10/2007 |

OTHER PUBLICATIONS

International Search Report for PCT Patent App. No. PCT/JP2008/060528 (Aug. 26, 2008).
Supplementary Partial European Search Report for EP 08 76 5329 dated Oct. 11, 2010.

* cited by examiner

Primary Examiner — James J Seidleck
Assistant Examiner — Deve E Valdez
(74) Attorney, Agent, or Firm — Kenealy Vaidya LLP

(57) ABSTRACT

A pharmaceutical/medical rubber compound contains the following components: (A) a composition obtainable by crosslinking (a) 100 parts by weight of an isobutylene polymer having terminal alkenyl groups with (d) a hydrosilyl-containing compound in the presence of (b) from 5 to 100 parts by weight of a polyolefin and (c) from 5 to 100 parts by weight of polybutene during melt kneading, and (B) an ultra-high molecular weight polyethylene powder. Compared with conventional thermoplastic elastomers, the pharmaceutical/medical rubber compound and its molded article are free from deformations and have sufficient permanent set resistance even under high temperature conditions, have excellent mechanical properties, low water absorption property, low reactivity and superb gas barrier properties, and can withstand high-temperature sterilization.

10 Claims, No Drawings

RUBBER COMPOUND AND MOLDED ARTICLE

TECHNICAL FIELD

This application is a U.S. national phase filing under 35 U.S.C.§371 of PCT Application No. PCT/JP2008/060528, filed Jun. 9, 2008, which claims priority under 35 U.S.C.§119 to Japanese Patent Application No. 2007-192930 filed on Jul. 25, 2007, the entire disclosures of which being incorporated herein, and to which priority is hereby claimed.

The presently disclosed subject matter relates to a pharmaceutical/medical rubber compound excellent in compression permanent set, heat resistance, gas barrier properties and the like, and also, to a molded or otherwise formed (hereinafter collectively referred to as "molded") article of the compound.

BACKGROUND ART

As chief materials in pharmaceutical/medical rubber compounds represented by pharmaceutical/medical containers and sealable articles, plasticizedpolyvinyl chloride resin, and natural rubber, butyl rubber, isoprene rubber, styrene-butadiene rubber and the like have been used conventionally.

Plasticized polyvinyl chloride resin is excellent in softness and flexibility, but on the other hand, is accompanied by such problems that a plasticizer may bleed out and that ethylene oxide may remain upon sterilization with ethylene oxide. On the other hand, the use of the latter rubber materials involves such problems that large equipment is needed as they generally require a vulcanization step and that a crosslinking agent may dissolve out. To lessen these problems, Patent Document 1, for example, proposes pharmaceutical/medical articles made of a block copolymer of an aromatic vinyl compound and isobutylene, and further, Patent Document 2 proposes pharmaceutical/medical containers made of a similar block copolymer as described above.

Patent Document 1: JP-A-5-212104
Patent Document 2: JP-A-5-269201

These block copolymers permit injection molding and require no crosslinking step, so that they are superior in moldability and economy to conventional rubber materials. Moreover, no crosslinking agent or the like is used, and therefore, the problem of its dissolution into medicaments has been resolved. Molded rubber articles according to the technologies proposed in the above-described Patent Documents 1 and 2 are, however, still accompanied by a serious problem in that they undergo significant permanent set under stress especially at high temperatures (during drying, sterilization treatment or the like). In addition, they are insufficient in rubber elasticity and are brittle even at room temperature, and are not sufficient either in inertness with medicaments.

DISCLOSURE

Examples of Problems to be Solved by the Disclosed Subject Matter

An aspect of the disclosed subject matter is, therefore, to solve the above-described problems, and to provide a pharmaceutical/medical rubber compound and its molded article, which compared with conventional thermoplastic elastomers, are free from deformations and have sufficient permanent set resistance even under high temperature conditions, have excellent mechanical properties, low water absorption property, low reactivity and superb gas barrier properties, and can withstand high-temperature sterilization.

Exemplary Means for Solving the Problems

The above-described aspect can be achieved by the disclosed subject matter to be described hereinafter. Described specifically, the presently disclosed subject matter provides a pharmaceutical/medical rubber compound comprising the following components: (A) a composition obtainable by crosslinking (a) 100 parts by weight of an isobutylene polymer having terminal alkenyl groups with (d) a hydrosilyl-containing compound in the presence of (b) from 5 to 100 parts by weight of a polyolefin and (c) from 5 to 100 parts by weight of polybutene during melt kneading, and (B) an ultra-high molecular weight polyethylene powder.

In the presently disclosed subject matter as described above, the polyolefin can be at least one polyolefin selected from polypropylene and polyethylene, that the polybutene has a number average molecular weight of from 700 to 2,000, that the ultra-high molecular weight polyethylene powder has an average particle size of from 10 to 100 µm, and/or that the pharmaceutical/medical rubber compound comprises from 2 to 20 parts by weight of the component (B) per 100 parts by weight of the component (A).

In the pharmaceutical/medical rubber compound according to the presently disclosed subject matter, the pharmaceutical/medical rubber compound can further comprise from 1 to 50 parts by weight of a styrene-based thermoplastic elastomer as component (C) per 100 parts by weight of the component (A). The styrene-based thermoplastic elastomer may have a weight average molecular weight of from 5,000 to 500,000.

The presently disclosed subject matter also provides a molded, pharmaceutical/medical rubber article, which is obtainable from the above-described rubber compound according to the presently disclosed subject matter and permits autoclave treatment. The molded article may have an external appearance that presents a white color or milky white color.

Examples of Advantageous Effects of the Disclosed Subject Matter

According to the presently disclosed subject matter, it is possible to provide a pharmaceutical/medical rubber compound and its molded article, which compared with use of conventional thermoplastic elastomers, are free from deformations and have sufficient permanent set resistance even under high temperature conditions, have excellent mechanical properties, low water absorption property, low reactivity and superb gas barrier properties, and can withstand high-temperature sterilization.

EXEMPLARY EMBODIMENTS OF THE DISCLOSED SUBJECT MATTER

The presently disclosed subject matter will next be described in further detail based on some exemplary embodiments for carrying out the disclosed subject matter. The term "isobutylene polymer having terminal alkenyl groups" as the component (a) in the presently disclosed subject matter means a polymer in which units derived from isobutylene account for 50 wt % or more, preferably 70 wt % or more, more preferably 90 wt % or more and terminal alkenyl groups are contained. As a monomer (monomers) other than isobutylene, no particular limitation is imposed thereon insofar as it is (they are) cationically-polymerizable monomer component(s). For example, monomers such as aromatic vinyl compounds, aliphatic olefins, dienes such as isoprene, butadiene and divinylbenzene, vinyl ethers, and β-pinene can be exemplified. They may be used singly, or two or more of them may be used in combination.

No particular limitation is imposed on the molecular weight of the component (a), but from 5,000 to 500,000 is preferred, with from 10,000 to 200,000 being particularly preferred, in terms of weight average molecular weight by GPC measurement (as determined using a polystyrene standard). A weight average molecular weight lower than 5,000 has a tendency of failing to fully exhibit mechanical properties and the like on molded articles, while a weight average molecular weight higher than 500,000 has a tendency of having lowered melt kneadability, and also, reduced reactivity upon crosslinking.

No particular limitation is imposed on the alkenyl groups in the component (a) in the presently disclosed subject matter insofar as they are groups each containing a carbon-carbon double bond which has activity to the crosslinking reaction by the hydrosilyl-containing compound. Specific examples include unsaturated aliphatic hydrocarbon groups such as vinyl, allyl, methylvinyl, propenyl, butenyl, pentenyl, and hexenyl; and unsaturated cyclic hydrocarbon groups such as cyclopropenyl, cyclobutenyl, cyclopentenyl, and cyclohexenyl.

As a method for introducing terminal alkenyl groups onto the component (a) in the presently disclosed subject matter, there is a method that as disclosed in JP-A-3-152164 and JP-A-7-304909, reacts a compound having an unsaturated group with a polymer having functional groups such as hydroxyl groups to introduce unsaturated groups onto the polymer. To introduce unsaturated groups onto a polymer having halogen atoms, on the other hand, there is a method that conducts a Friedel-Crafts reaction with an alkenyl phenyl ether, a method that conducts a substitution reaction with allyltrimethylsilane or the like in the presence of a Lewis acid, or a method that conducts a Friedel-Crafts reaction with one of various phenols to introduce hydroxyl groups and then conducts the above-described alkenyl-introducing reaction. Of these methods, preferred from the standpoint of reactivity is the method that introduces terminal allyl groups by the substitution reaction between allyltrimethylsilane and chlorine.

The amount of alkenyl groups in the component (a) in the presently disclosed subject matter can be chosen as desired depending on the properties required for a molded article. From the viewpoint of properties after the crosslinking, however, a polymer containing at an end or ends thereof at least 0.2 alkenyl group on average per molecule is preferred, one containing 1.0 or more alkenyl groups on average per molecule being more preferred, and one containing 1.5 or more alkenyl groups on average per molecule being most preferred. If fewer than 0.2 alkenyl group is contained on average per molecule, there is a potential problem that the crosslinking reaction may not proceed fully.

As the polyolefin as the component (b) in the presently disclosed subject matter, it is possible to use one of or a combination of two or more of homopolymers, random copolymers and block copolymers of α-olefins, and mixtures thereof; random copolymers, block copolymers and graft copolymers of α-olefins and other unsaturated monomers; and oxidized, halogenated or sulfonated derivatives of these polymers. Specific examples include polyethylene resins such as polyethylene, ethylene-propylene copolymer, ethylene-propylene-non-conjugated diene copolymer, ethylene-butene copolymer, ethylene-hexene copolymer, ethylene-octene copolymer, ethylene-vinyl acetate copolymer, ethylene-vinyl alcohol copolymer, ethylene-ethyl acrylate copolymer, ethylene-acrylic acid copolymer, ethylene-methyl acrylate-maleic anhydride, and chlorinated polyethylene; polypropylene resins such as polypropylene, propylene-ethylene random copolymer, propylene-ethylene block copolymer, and chlorinated polypropylene; and poly-1-butene, polyisobutylene, polymethylpentene, (co)polymers of cyclic olefins and the like.

Among these, polyethylene, polypropylene or a mixture thereof can be preferably used from the standpoints of cost and balanced properties. Illustrative of polyethylene include high-density polyethylene, low-density polyethylene, linear low-density polyethylene, and the like, and illustrative of polypropylene include homopolypropylene, random polypropylene, block polypropylene, and the like. Of these, polypropylene is most preferred from the standpoint of heat resistance. No particular limitation is imposed on the melt flow rate (MFR) of polyolefin to be used, but from the standpoint of molding fluidity, from 0.1 to 100 (g/10 min) is preferred, with from 1 to 100 (g/10 min) being more preferred.

In the presently disclosed subject matter, the component (b) not only functions as a crosslinking reaction site for the component (a), but also acts to impart molding fluidity, heat resistance, mechanical strength, slidability and the like to the final rubber composition. The amount of the component (b) to be added is set at from 5 to 100 parts by weight per 100 parts by weight of the component (a), with from 5 to 80 parts by weight being more preferred, and from 10 to 50 parts by weight being most preferred. An amount of the component (b) smaller than 5 parts by weight has a tendency of failing to provide sufficient molding fluidity, while an amount of the component (b) greater than 100 parts by weight has a tendency of being impaired in softness and failing to fully exhibit sealing property.

Polybutene as the component (c) in the presently disclosed subject matter is used to provide a molded article, which is to be produced from the rubber compound according to the presently disclosed subject matter, with excellent gas barrier properties, softness, fluidity and the like. Component (c) can be one having properties such as low dissolution property and low impurity property. As such a component (c), one available from the market, for example, under the trade name of "IDEMITSU POLYBUTENE 100R" (product of Idemitsu Kosan Co., Ltd.) or the like can be used. Polybutene is particularly superior in the presently disclosed subject matter, because polybutene minimizes a reduction in the gas barrier properties of polyisobutylene (PIB) and undergoes very little dissolution-out and bleed-out although the addition of a softening agent generally impairs the excellent gas barrier properties of PIB and dissolution-out and bleed-out of the softening agent is unavoidable. These physical properties are especially important as a rubber material for pharmaceutical/medical applications.

The amount of the component (c) to be used may be in the range of from 5 to 100 parts by weight per 100 parts by weight of the component (a). A use amount of the component (c) smaller than 5 parts by weight may not be able to provide the resulting molded rubber article with reduced hardness and may also lead to insufficient gas barrier properties in some instances. On the other hand, a use amount of the component (c) greater than 100 parts by weight may provide the resulting molded rubber article with tackiness or may result in the recognition of dissolution-out and/or bleed-out on the resulting molded rubber article. Further, a number average molecular weight of the component (c) lower than 700 results in the recognition of dissolution-out and/or bleed-out, while a number average molecular weight of the component (c) higher than 2,000 is less effective as a softening agent.

In the presently disclosed subject matter, the hydrosilyl-containing compound (d) is used as a crosslinking agent for the component (a). No particular limitation is imposed on the usable hydrosilyl-containing compound. However, a hydrosilyl-containing polysiloxane can be used, and various hydrosilyl-containing polysiloxanes can be used. Among these, preferred are hydroxysilyl-containing polysiloxanes having 3 or more hydrosilyl groups and 3 or more but 500 or less siloxane units, more preferred are hydroxysilyl-containing polysiloxanes having 3 or more hydrosilyl groups and 10 or more but 200 or less siloxane units, and more preferred are hydroxysilyl-containing polysiloxanes having 3 or more hydrosilyl groups and 20 or more but 100 or less siloxane units.

Less than 3 hydrosilyl groups have a tendency of failing to achieve sufficient growth of a network by crosslinking and to obtain optimal rubber elasticity, and more than 500 siloxane units have a tendency of providing the polysiloxane with high viscosity and reduced dispersibility in the component (a) and causing the crosslinking reaction to proceed insufficiently. The term "polysiloxane units" as used herein indicates units represented by the following formulas (I), (II) and (III):

Usable as a hydroxysilyl-containing polysiloxane is a compound such as a linear polysiloxane represented by the following formula (IV) or (V):

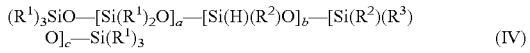

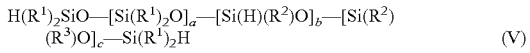

wherein $R^1$ and $R^2$ represent a $C_{1-6}$ alkyl group or phenyl group, $R^3$ represents a $C_{1-10}$ alkyl group or aralkyl group, b is equal to or greater than 3, and a, b and c denote integers satisfying $3 \leq a+b+c \leq 500$, or a cyclic siloxane represented by the following formula (VI):

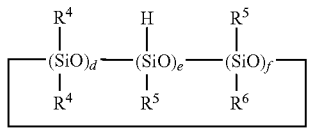

wherein $R^4$ and $R^5$ represent a $C_{1-6}$ alkyl group or phenyl group, $R^6$ represents a $C_{1-10}$ alkyl group or aralkyl group, e is equal to or greater than 3, and d, e and f denote integers satisfying $d+e+f \leq 500$.

The component (a) and the hydrosilyl-containing compound can be mixed together at a desired ratio, but from the aspect of the crosslinking rate, the ratio of hydrosilyl groups to alkenyl groups (hydrosilyl groups/alkenyl groups) may be preferably in a range of from 0.5 to 10, particularly preferably from 1 to 5, in terms of molar ratio. A molar ratio smaller than 0.5 tends to lead to insufficient crosslinking, while a molar ratio greater than 10 results in a great deal of active hydrosilyl groups still remaining even after crosslinking, and therefore, tends to produce volatiles.

The crosslinking reaction between the component (a) and the component (d) are allowed to proceed when these two components are mixed together and are then heated. To allow the reaction to proceed more rapidly, addition of a hydrosilylating catalyst can be used. No particular limitation is imposed on such a hydrosilylating catalyst. For example, a radical generator such as an organic peroxide or azo compound, or a transition metal catalyst can be mentioned.

No particular limitation is imposed on the radical generator. Examples include dialkyl peroxides such as di-t-butyl peroxide, 2,5-dimethyl-2,5-di(t-butylperoxy)hexane, 2,5-dimethyl-2,5-di(t-butylperoxy)-3-hexyne, dicumyl peroxide, t-butylcumyl peroxide, and α,α'-bis(t-butylperoxy)isopropylbenzene; diacyl peroxides such as benzoyl peroxide, p-chlorobenzoyl peroxide, m-chlorobenzoyl peroxide, 2,4-dichlorobenzoyl peroxide, and lauroyl peroxide; peracid esters such as t-butyl perbenzoate; peroxydicarbonates such as diisopropyl perdicarbonate and di(2-ethylhexyl)perdicarbonate; and peroxyketals such as 1,1-di(t-butylperoxy)cyclohexane and 1,1-di(t-butylperoxy)-3,3,5-trimethylcyclohexane.

No particular limitation is imposed either on the transition metal catalyst. Examples include elemental platinum; catalyst obtained by dispersing solid platinum on carriers such as alumina, silica and carbon black; chloroplatinic acid; complexes between chloroplatinic acid and alcohols, aldehydes and ketones; and platinum-olefin complexes, and platinum (0)-dialkenyltetramethyldisiloxane complexes. As examples of catalysts other than platinum compounds, $RhCl(PPh_3)_3$, $RhCl_3$, $RuCl_3$, $IrCl_3$, $FeCl_3$, $AlCl_3$, $PdCl_2 \cdot H_2O$, $NiCl_2$, $TiCl_4$ and the like can be mentioned. These catalysts can be used singly, or two or more of them can be used in combination. Among these, platinum vinylsiloxane is most preferred from the standpoint of crosslinking efficiency.

No particular limitation is imposed on the amount of the catalyst. The catalyst may, however, be used preferably in a range of from $10^{-1}$ to $10^{-8}$ mol, more preferably in a range of from $10^{-3}$ to $10^{-6}$ mol per mol of the alkenyl groups in the component (a). An amount of the catalyst smaller than $10^{-8}$ mol tends to result in an insufficient progress of the crosslinking, while an amount of the catalyst greater than $10^{-1}$ mol tends to result in strong evolution of heat so that the crosslinking reaction may not be fully controlled.

In the presently disclosed subject matter, the component (a) is dynamically crosslinked with the component (d) in the presence of the component (b) and component (c) during melt kneading. As the melt kneading temperature, a temperature of from 130 to 240° C. can be used. A temperature lower than 130° C. tends to result in insufficient melting of the component (b), and hence, to lead to non-uniform kneading. A temperature higher than 240° C., on the other hand, tends to cause thermal decomposition of the component (a). No particular limitation is imposed on the melt-kneading method, and a known method can be applied. For example, the component (a) and component (b), and further, the crosslinking agent and a crosslinking catalyst, and other components, which may be added to obtain predetermined physical properties, can be subjected to melt kneading by using a heating header, for example, a single-screw extruder, twin-screw extruder, roll mixer, Banbury mixer, Brabender mixer, kneader or high-shear mixer to perform the production. As the order of their addition, it is possible to adopt a method that subsequent to melting of the component (b), the component (a) is added and other components are further added as needed, and after mixing them into a uniform melt, the crosslinking agent and crosslinking catalyst are added to allow the cross linking reaction to proceed.

The component (B) (ultra-high molecular weight polyethylene powder), which constitutes the rubber compound according to the presently disclosed subject matter, is a powder of an ultra-high molecular weight polyethylene the average molecular weight of which ranges from $1 \times 10^6$ to $6 \times 10^6$, and is available from the market, for example, under the trade name of "MIPELON" (product of Mitsui Chemicals, Inc.). It has been confirmed that the component (B) is effective in providing the rubber compound with improved shape retaining property at high temperatures, reducing surface tackiness and also providing the compound with improved fluidity, and also that its addition in an adequate amount is effective in providing the compound with improved coring characteristics. The component (B) can have an average particle size of from 10 to 100 μm (measurement method: observation under an electron microscope).

The amount of the component (B) to be used may be in a range of from about 2 to 20 parts by weight per 100 parts by weight of the component (A). A use amount of the component (B) smaller than about 2 parts by weight results in a molded rubber article with impaired shape retaining property, while a use amount of the component (B) greater than about 20 parts by weight leads to a molded rubber article with impaired softness and hence with reduced functions such as coring and fluid leakage.

In the presently disclosed subject matter, the component (A) and component (B) are essential. For providing the rubber compound of the presently disclosed subject matter with improved moldability, it is possible to add a styrene-based thermoplastic elastomer as a component (C) in an amount of from 1 to 50 parts by weight per 100 parts by weight of the component (A). Examples of the styrene-based thermoplastic elastomer include styrene-butadiene-styrene block copolymer (SBS), styrene-isoprene-styrene block copolymer (SIS), styrene-ethylene butylene-styrene block copolymer (SEBS), styrene-ethylene propylene-styrene block copolymer (SEPS), styrene-isobutylene-styrene block copolymer (SIBS), and the like.

Further, one or more of various thermoplastic resins and various additives can also be added to extent not interfering with the aspect of the presently disclosed subject matter. Illustrative of the thermoplastic resins include polyolefin resins, polyphenylene ether resins, aromatic vinyl compound resins, polycarbonate resins, polyamide resins, vinyl chloride resins, styrene-based block copolymers (for example, butadiene-styrene block copolymer, styrene-isobutylene block copolymer), butadiene-isoprene block copolymer, and their hydrogenated products.

The additives include stabilizers such as antioxidants and ultraviolet absorbers; and aids such as lubricants, plasticizers, dyes, pigments, flame retardants, fillers, reinforcements, tackifiers, and the like. The fillers and reinforcements include glass fibers, carbon black, flake graphite, carbon fibers, calcium sulfate, calcium carbonate, calcium silicate, alumina, silica, titanium oxide, talc, mica, and the like.

The molded rubber article according to the presently disclosed subject matter can be obtained by molding the above-described rubber compound of the presently disclosed subject matter in accordance with a known method, for example, injection molding, extrusion, compression molding, calendaring or the like. Examples of the molded article include rubber closures for medicines, syringe gaskets, syringe caps, rubber closures for blood collecting tubes, and the like, with rubber closures being particularly well suited. These molded articles are free from deformations and have sufficient permanent set resistance even under high temperature conditions, have excellent mechanical properties, low water absorption property, low reactivity and superb gas barrier properties, and can withstand high-temperature sterilization. Moreover, sterilization by electron beam or radiation is also feasible.

The molded rubber article according to the presently disclosed subject matter may be formed into a molded rubber article with a laminate film stacked on a surface thereof. The material of the laminate film can be an ultra-high molecular weight polyethylene or fluorinated resin. Preferred is a fluorinated resin, and especially preferred is polytetrafluoroethylene (PTFE). The formation of the molded rubber article of the presently disclosed subject matter into a laminated molded article makes it possible to reduce the tackiness at the surface of the molded rubber article and a chemical reaction between the rubber and a medical solution and also to provide the molded rubber article with improved high-temperature shape retaining property. Examples of the molded rubber article according to the presently disclosed subject matter include, but are not limited to, rubber closures for sealing mouth portions of containers such as vials, syringe pistons, and nozzle caps for sealing nozzle portions of syringes.

EXAMPLES

The presently disclosed subject matter will next be described more specifically based on Examples and Comparative Examples.

Examples 1-26 & Comparative Examples 1-3

Rubber compounds of these Examples and Comparative Examples were produced by kneading the corresponding components shown below in Table 1-1 to Table 1-3 (the figures in the tables indicate amounts in parts by weight) at 200° C. and 200 rpm in a twin-screw extruder.

It is to be noted that in Examples 1-10 and 21-24 and Comparative Example 2, the following commercial product was used as the composition of the component (A).

Composition of the component (A) (trade name: "SIBSTAR P1140B", product of Kaneka Corporation) [(a)/(b)/(c)/(d)=100/11/40/1.2 (parts by weight)]
(a) (PIB): an isobutylene polymer having terminal alkenyl groups (produced following Production Example 1 of WO-A-2006/098142, weight average molecular weight: 50,000)
(b) (polyolefin): random polypropylene (r-PP) (trade name: "PRIME POLYPRO J215W", product of Prime Polymer Co., Ltd., MFR: 9)
(c) (polybutene-based oil): (trade name: "IDEMITSU POLYBUTENE 100R", product of Idemitsu Kosan Co., Ltd., number average molecular weight: 960)
(d) (crosslinking agent): A hydrosilyl-containing polysiloxane represented by the following chemical formula (1) was used.

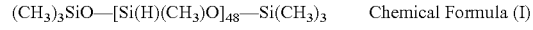

$(CH_3)_3SiO—[Si(H)(CH_3)O]_{48}—Si(CH_3)_3$　　　Chemical Formula (I)

As the composition of the component (A) in Examples 11-20, 25 and 26, "SIBSTARE1140B" (trade name) was used, which was the same as the component (A) in Example 1, etc. except that as the component (b), high-density polyethylene (HDPE) (trade name: "HI-ZEX 2200)", product of Prime Polymer Co., Ltd., MFR: 5.2) was used in place of the random polypropylene.

In Comparative Example 1, was used "SIBSTAR E1140" (trade name, product of Kaneka Corporation; (a)/(b)/(c)=100/11/40 (parts by weight), the component (b): high-density polyethylene (HDPE) (trade name: "HI-ZEX 2200)", product of Prime Polymer Co., Ltd., MFR: 5.2), the component (c): paraffin-based oil (trade name: "JOMO PROCESS P500", product of Japan Energy Corporation).

As the component (B) in all the Examples and Comparative Examples, an ultra-high molecular weight polyethylene powder (UHMWPE) (trade name: "MIPELON 220", product of Mitsui Chemicals, Inc., average particle size: 20 μm) was used.

The above-described compounds of Examples 1-26 and Comparative Examples 1-3 were each tested for compression permanent set, hardness, gas barrier properties, softening point and others by the below-described testing methods, and the results shown below in Table 2-1 to Table 2-3 were obtained.

[Measuring Methods]

1. Compression Permanent Set (Test 1)

TABLE 1-1

(Figures in the table indicate amounts in parts by weight)

| | Examples | | | | | | | | | |
|---|---|---|---|---|---|---|---|---|---|---|
| | 1 | 2 | 3 | 4 | 5 | 6 | 7 | 8 | 9 | 10 |
| PIB (a) | 100 | 100 | 100 | 100 | 100 | 100 | 100 | 100 | 100 | 100 |
| SEBS (C) | — | — | — | — | 5 | 20 | 50 | — | — | — |
| SIBS (C) | — | — | — | — | — | — | — | 5 | 20 | 50 |
| Polybutene-based oil (c) | 40 | 40 | 40 | 40 | 40 | 40 | 40 | 40 | 40 | 40 |
| Paraffin-based oil (c) | — | — | — | — | — | — | — | — | — | — |
| r-PP (b) | 11 | 11 | 11 | 11 | 11 | 11 | 11 | 11 | 11 | 11 |
| HDPE (b) | — | — | — | — | — | — | — | — | — | — |
| UHMWPE (B) | 2 | 5 | 10 | 20 | 5 | 5 | 5 | 5 | 5 | 5 |
| Crosslinking agent (d) | 1.2 | 1.2 | 1.2 | 1.2 | 1.2 | 1.2 | 1.2 | 1.2 | 1.2 | 1.2 |

SEBS: "SEPTON 8076", trade name; product of Kuraray Co., Ltd. (styrene content: 30 wt %)
SIBS: "SIBSTAR 103T", trade name; product of Kaneka Corporation (styrene content: 30 wt %, weight average molecular weight: 100,000)

TABLE 1-2

(Figures in the table indicate amounts in parts by weight)

| | Examples | | | | | | | | | |
|---|---|---|---|---|---|---|---|---|---|---|
| | 11 | 12 | 13 | 14 | 15 | 16 | 17 | 18 | 19 | 20 |
| PIB (a) | 100 | 100 | 100 | 100 | 100 | 100 | 100 | 100 | 100 | 100 |
| SEBS (C) | — | — | — | — | 5 | 20 | 50 | — | — | — |
| SIBS (C) | — | — | — | — | — | — | — | 5 | 20 | 50 |
| Polybutene-based oil (c) | 40 | 40 | 40 | 40 | 40 | 40 | 40 | 40 | 40 | 40 |
| Paraffin-based oil (c) | — | — | — | — | — | — | — | — | — | — |
| r-PP (b) | — | — | — | — | — | — | — | — | — | — |
| HDPE (b) | 11 | 11 | 11 | 11 | 11 | 11 | 11 | 11 | 11 | 11 |
| UHMWPE (B) | 2 | 5 | 10 | 20 | 5 | 5 | 5 | 5 | 5 | 5 |
| Crosslinking agent (d) | 1.2 | 1.2 | 1.2 | 1.2 | 1.2 | 1.2 | 1.2 | 1.2 | 1.2 | 1.2 |

SEBS: "SEPTON 8076", trade name; product of Kuraray Co., Ltd. (styrene content: 30 wt %)
SIBS: "SIBSTAR 103T", trade name; product of Kaneka Corporation (styrene content: 30 wt %, weight average molecular weight: 100,000)

TABLE 1-3

(Figures in the table indicate amounts in parts by weight)

| | Examples | | | | | | Comp. Exs. | | |
|---|---|---|---|---|---|---|---|---|---|
| | 21 | 22 | 23 | 24 | 25 | 26 | 1 | 2 | 3 |
| PIB (a) | 100 | 100 | 100 | 100 | 100 | 100 | 100 | 100 | — |
| SEBS (C) | — | — | 55 | — | 55 | — | — | — | 100 |
| SIBS (C) | — | — | — | 55 | — | 55 | — | — | — |
| Polybutene-based oil (c) | 40 | 40 | 40 | 40 | 40 | 40 | — | 40 | 40 |
| Paraffin-based oil (c) | — | — | — | — | — | — | 40 | — | — |
| r-PP (b) | 11 | 11 | 11 | 11 | — | — | — | 11 | 11 |
| HDPE (b) | — | — | — | — | 11 | 11 | 11 | — | — |
| UHMWPE (B) | 1 | 25 | 5 | 5 | 5 | 5 | 5 | — | 5 |
| Crosslinking agent (d) | 1.2 | 1.2 | 1.2 | 1.2 | 1.2 | 1.2 | 1.2 | 1.2 | — |

SEBS: "SEPTON 8076", trade name; product of Kuraray Co., Ltd. (styrene content: 30 wt %)
SIBS: "SIBSTAR 103T", trade name; product of Kaneka Corporation (styrene content: 30 wt %, weight average molecular weight: 100,000)

Each sample was measured in accordance with JIS K 6262: 2006.

2. Softening Point (° C.) (Test 2)

Each sample was measured using a thermal analyzer ("DSC8230", manufactured by Rigaku Corporation).

3. Oxygen Barrier Properties ($cm^3/m^2 \cdot 24h \cdot atm$) (Test 3)

Each sample was formed into a plate of 0.5 mm thickness, and then measured in compliance with JIS K 7126-1:2006.

4. Surface Conditions (Touch Observation) (Test 4)

Each formed sample was touched with a finger to determine whether or not its surface was tacky.

5. Autoclave Resistance Test (Test 5)

With each sample molded into the form of a rubber closure, a 10-mL vial filled with 10 mL of distilled water was capped. An aluminum cap was applied, and then wrapped up by a hand crimper (hand-operated wrap-up tool) to seal the vial. The vial was placed in an autoclave, and subjected to hydrothermal treatment at 121° C. for 60 minutes. After the treatment, the aluminum cap was removed to determine the state of deformation of the rubber closure. Assessment standards were set as follows:

A: Absolutely no change in shape was observed in external appearance.
B: A slight change in shape was observed, but no problem was caused.
C: A change in the shape of a rubber closure was observed, and there was a room for improvements.

6. Chemical Test (Preparation of Test Solutions)

As a test sample for this test, rubber closures made of each sample were weighed (total weight: about 20 g) in a clean beaker of 300 mL capacity, to which 10-fold volumes of distilled water were added. The beaker was loosely covered at a top part thereof with an appropriate lid, placed in an autoclave, and then heated at 121° C. for 60 minutes. The beaker was immediately taken out of the autoclave, and after allowed to stand at room temperature, the resulting dissolved solution of the sample was provided as a test solution.

(Testing Method)

The prepared test solution (the water-dissolved solution of each sample) was assessed for solution quality (potassium permanganate consumption (mL) (Chemical Test 1), a difference in pH value (a difference from a blank value) (Chemical Test 2), absorbance of ultraviolet light (220 nm/350 nm) (Chemical Test 3), and transmittance of visible light (450 nm/659 nm (%)) (Chemical Test 4) in compliance with the Japanese Pharmacopoeia (15$^{th}$ edition), Testing Method for Rubber Closures for Aqueous Infusion, Test for Dissolved Substances.

7. Physical Tests (1) Hardness (JIS A type (degree)) (Physical Test 1)

Each sample was formed into a plate of 2 mm thickness, and its measurement was conducted following JIS K 6253: 1997.

(2) Liquid Leakage Test (mL) (Physical Test 2)

Aliquots (10 mL) of water were placed in 10-mL vials, respectively. The vials were capped with rubber closures made of the respective samples. An aluminum cap was applied to each capped vial, and then wrapped up by a hand crimper to seal the vial. An over-cap portion of the aluminum cap was removed, and an 18 G hypodermic needle was fitted on a disposable syringe. Subsequent to drawal of air (2 mL), the hypodermic needle was caused to penetrate (was pierced) vertically through the sample rubber closure, and then, the above-mentioned air (2 mL) was injected into the vial. After the injection of the air, the vial was promptly held upside down, and the water (2 mL) was drawn. The hypodermic needle was gently pulled out, and the weight of the liquid leaked out subsequently was measured. As a general acceptable value, the total leakage is 0.1 mL (0.1 g) or less.

(3) Coring Test (Number of Fallen-Off Pieces/Total Number of Needle Penetrations) (Physical Test 3)

Aliquots (10 mL) of water were placed in vials (commercial products) having a specification capacity of 10 mL, and the vials were capped with the respective samples (pharmaceutical rubber closures). An aluminum cap was applied to each capped vial, and then wrapped up by a hand crimper to seal the vial. An over-cap portion of the aluminum cap was removed, and an 18G hypodermic needle was fitted on a disposable syringe. Subsequent to drawal of water (2 mL), the hypodermic needle was caused to penetrate (was pierced) vertically four times at random through the sample rubber closure. Subsequently, the water inside the syringe was injected into the vial, and the hypodermic needle was pulled out. After the vial was shaken up and down several times, the number of fallen-off pieces of the sample rubber closure in the vial was counted. At the same time, the sample rubber closure was also visually observed for its surface conditions under a microscope to determine the existence or absence of traces (of fall-off). As a general acceptable value, the number of fallen-off pieces from each sample (pharmaceutical rubber closure) is 2 pieces or fewer when pierced 40 times at random.

8. Assessment of Rubber Closures

Assessments of each rubber closure for chemical compatibility and functionality were performed in accordance with the following three-stage assessment procedure.

Three-stage assessment procedure:
A: Superior to specification value
B: Not compatible with specification value
C: Very inferior to specification value

TABLE 2-1

| Tests/ assessments | Examples | | | | |
|---|---|---|---|---|---|
| | 1 | 2 | 3 | 4 | 5 |
| Test 1 | 23 | 26 | 27 | 30 | 26 |
| Test 2 | 138 | 138 | 136 | 138 | 136 |
| Test 3 | 160 | 160 | 172 | 180 | 162 |
| Test 4 | Non-tacky | | | | |
| Test 5 | B | A | A | A | A |
| Tests by official methods (The Japanese Pharmacopeia) | | | | | |
| Chemical Test 1 | 0.07 | 0.05 | 0.03 | 0.06 | 0.08 |
| Chemical Test 2 | 0.02 | 0.02 | 0.01 | 0.00 | −0.01 |
| Chemical Test 3 | 0.005 | 0.002 | 0.004 | 0.002 | 0.007 |
| Chemical Test 4 | 100.0/100.0 | | | | |
| Physical Test 1 | 33 | 34 | 40 | 42 | 41 |
| Physical Test 2 | 0.03 | 0.04 | 0.07 | 0.07 | 0.08 |
| Physical Test 3 | 0/40 | 0/40 | 1/40 | 1/40 | 1/40 |
| Chemical compatibility test | A | A | A | A | A |
| Assessment of functionality | A | A | A | A | A |

| Tests/ assessments | Examples | | | | |
|---|---|---|---|---|---|
| | 6 | 7 | 8 | 9 | 10 |
| Test 1 | 23 | 25 | 28 | 30 | 33 |
| Test 2 | 137 | 134 | 136 | 135 | 134 |
| Test 3 | 180 | 200 | 163 | 162 | 163 |
| Test 4 | Non-tacky | | | | |
| Test 5 | A | A | A | A | B |
| Tests by official methods (The Japanese Pharmacopeia) | | | | | |
| Chemical Test 1 | 0.09 | 0.11 | 0.04 | 0.05 | 0.05 |
| Chemical Test 2 | −0.05 | −0.01 | 0.01 | 0.00 | 0.01 |

TABLE 2-1-continued

| | | | | | |
|---|---|---|---|---|---|
| Chemical Test 3 | 0.008 | 0.007 | 0.003 | 0.004 | 0.007 |
| Chemical Test 4 | | | 100.0/100.0 | | |
| Physical Test 1 | 33 | 36 | 34 | 35 | 37 |
| Physical Test 2 | 0.02 | 0.02 | 0.03 | 0.02 | 0.07 |
| Physical Test 3 | 0/40 | 2/40 | 1/40 | 0/40 | 1/40 |
| Chemical compatibility test | A | A | A | A | A |
| Assessment of functionality | A | A | A | A | A |

TABLE 2-2

| Tests/ assessments | Examples | | | | |
|---|---|---|---|---|---|
| | 11 | 12 | 13 | 14 | 15 |
| Test 1 | 24 | 25 | 27 | 31 | 28 |
| Test 2 | 132 | 133 | 132 | 131 | 133 |
| Test 3 | 164 | 167 | 174 | 180 | 168 |
| Test 4 | | | Non-tacky | | |
| Test 5 | B | B | B | B | B |
| Tests by official methods (The Japanese Pharmacopeia) | | | | | |
| Chemical Test 1 | 0.05 | 0.06 | 0.03 | 0.03 | 0.07 |
| Chemical Test 2 | 0.01 | 0.03 | 0.00 | 0.01 | −0.03 |
| Chemical Test 3 | 0.002 | 0.004 | 0.003 | 0.005 | 0.008 |
| Chemical Test 4 | | | 100.0/100.0 | | |
| Physical Test 1 | 30 | 32 | 37 | 40 | 38 |
| Physical Test 2 | 0.04 | 0.04 | 0.05 | 0.06 | 0.02 |
| Physical Test 3 | 0/40 | 0/40 | 0/40 | 1/40 | 1/40 |
| Chemical compatibility test | A | A | A | A | A |
| Assessment of functionality | A | A | A | A | A |

| Tests/ assessments | Examples | | | | |
|---|---|---|---|---|---|
| | 16 | 17 | 18 | 19 | 20 |
| Test 1 | 23 | 25 | 29 | 31 | 33 |
| Test 2 | 131 | 130 | 131 | 132 | 131 |
| Test 3 | 185 | 208 | 169 | 167 | 165 |
| Test 4 | | | Non-tacky | | |
| Test 5 | B | B | B | B | B |
| Tests by official methods (The Japanese Pharmacopeia) | | | | | |
| Chemical Test 1 | 0.10 | 0.12 | 0.05 | 0.05 | 0.05 |
| Chemical Test 2 | −0.01 | −0.03 | 0.00 | 0.01 | −0.01 |
| Chemical Test 3 | 0.009 | 0.008 | 0.003 | 0.004 | 0.005 |
| Chemical Test 4 | | | 100.0/100.0 | | |
| Physical Test 1 | 42 | 36 | 33 | 35 | 36 |
| Physical Test 2 | 0.03 | 0.02 | 0.04 | 0.03 | 0.03 |
| Physical Test 3 | 0/40 | 2/40 | 0/40 | 1/40 | 1/40 |
| Chemical compatibility test | A | A | A | A | A |
| Assessment of functionality | A | A | A | A | A |

TABLE 2-3

| Tests/ assessments | Examples | | | | |
|---|---|---|---|---|---|
| | 21 | 22 | 23 | 24 | 25 |
| Test 1 | 27 | 32 | 24 | 37 | 25 |
| Test 2 | 134 | 134 | 137 | 132 | 131 |
| Test 3 | 158 | 188 | 240 | 162 | 260 |
| Test 4 | | | Non-tacky | | |
| Test 5 | B | A | A | C | B |
| Tests by official methods (The Japanese Pharmacopeia) | | | | | |
| Chemical Test 1 | 0.05 | 0.06 | 0.12 | 0.07 | 0.12 |
| Chemical Test 2 | −0.01 | 0.02 | −0.03 | 0.00 | −0.01 |
| Chemical Test 3 | 0.006 | 0.005 | 0.006 | 0.012 | 0.008 |
| Chemical Test 4 | 100.0/100.0 | | | 99.3/100.0 | 100.0/100.0 |
| Physical Test 1 | 32 | 48 | 35 | 37 | 41 |
| Physical Test 2 | 0.03 | 0.13 | 0.02 | 0.11 | 0.03 |
| Physical Test 3 | 1/40 | 3/40 | 1/40 | 2/40 | 2/40 |
| Chemical compatibility test | A | A | A | A | A |
| Assessment of functionality | B | B | B | B | B |

| Tests/ assessments | Ex. | Comparative Examples | | |
|---|---|---|---|---|
| | 26 | 1 | 2 | 3 |
| Test 1 | 37 | 24 | 24 | 32 |
| Test 2 | 130 | 120 | 128 | 122 |
| Test 3 | 164 | 610 | 148 | 320 |
| Test 4 | Non-tacky | | Slightly tacky | |
| Test 5 | C | C | C | C |
| Tests by official methods (The Japanese Pharmacopeia) | | | | |
| Chemical Test 1 | 0.08 | 0.37 | 0.04 | 0.92 |
| Chemical Test 2 | 0.01 | 2.6 | 0.00 | 0.40 |
| Chemical Test 3 | 0.007 | 0.089 | 0.008 | 99.1 |
| Chemical Test 4 | 99.1/100.0 | 93.8/97.1 | 100.0/100.0 | 99.3/100.0 |
| Physical Test 1 | 38 | 30 | 26 | 43 |
| Physical Test 2 | 0.08 | 0.04 | 0.04 | 0.08 |
| Physical Test 3 | 1/40 | 1/40 | 2/40 | 5/40 |
| Chemical compatibility test | A | C | A | B |
| Assessment of functionality | B | C | C | C |

As has been described above, molded, pharmaceutical/medical rubber articles excellent in high-temperature deformation properties, compression permanent set, hardness, water absorption property, reactivity, gas barrier properties, softening point and others can be obtained according to the presently disclosed subject matter. It is to be noted that, although the rubber compounds of Examples 21 to 26 are within a range usable for the intent of the presently disclosed subject matter, autoclave resistance is observed to have a tendency of being reduced when the component (B) decreases to less than 2 parts by weight while a molded article is confirmed to have a tendency of being reduced in softness and deteriorated in coring when the component (B) exceeds 20 parts by weight. Further, a molded article is observed to have a tendency of being reduced in oxygen barrier properties when SEBS as a component (C) exceeds 50 parts by weight, and a molded article can be confirmed to have a tendency of being reduced in autoclave resistance when SIBS as a component (C) exceeds 50 parts by weight.

INDUSTRIAL APPLICABILITY

According to the presently disclosed subject matter, it is possible to provide a pharmaceutical/medical rubber compound and its molded article, which compared with conventional thermoplastic elastomers, are free from deformations and have sufficient permanent set resistance even under high temperature conditions, have excellent mechanical properties, low water absorption property, low reactivity and superb gas barrier properties, and can withstand high-temperature sterilization.

The invention claimed is:
1. A pharmaceutical/medical rubber compound comprising the following components: (A) a composition obtained by crosslinking (a) 100 parts by weight of an isobutylene poly- mer having terminal alkenyl groups with (d) a hydrosilyl-containing compound in the presence of (b) from 5 to 100 parts by weight of a polyolefin per 100 parts by weight of the isobutylene polymer and (c) from 5 to 100 parts by weight of polybutene per 100 parts by weight of the isobutylene polymer during melt kneading, and (B) 2 to less than 20 parts by weight of an ultra-high molecular weight polyethylene powder per 100 parts by weight of the component (A).

2. The pharmaceutical/medical rubber compound according to claim 1, wherein the polyolefin is at least one polyolefin selected from polypropylene and polyethylene.

3. The pharmaceutical/medical rubber compound according to claim 1, wherein the polybutene has a number average molecular weight of from 700 to 2,000.

4. The pharmaceutical/medical rubber compound according to claim 1, wherein the ultra-high molecular weight polyethylene powder has an average particle size of from 10 to 100 μm.

5. The pharmaceutical/medical rubber compound according to claim 1, further comprising from 1 to 50 parts by weight of a component (C) per 100 parts by weight of the component (A), wherein the component (C) is a styrene based thermoplastic elastomer.

6. The pharmaceutical/medical rubber compound according to claim 5, wherein the styrene-based thermoplastic elastomer has a weight average molecular weight of from 5,000 to 500,000.

7. The pharmaceutical/medical rubber compound according to claim 1, which presents a white color 8. A molded, pharmaceutical/medical rubber article obtained by molding the rubber compound according to claim 1.

9. The pharmaceutical/medical rubber compound according to claim 1, wherein the molar ratio of hydrosilyl groups to alkenyl groups (hydrosilyl groups/alkenyl groups) is in a range of from 1 to 5.

10. The pharmaceutical/medical rubber compound according to claim 5, wherein the styrene based thermoplastic elastomer is at least one of a styrene-butadiene-styrene block copolymer (SBS), a styrene-isoprene-styrene block copolymer (SIS), a styrene-ethylene butylene-styrene block copolymer (SEBS), a styrene-ethylene propylene-styrene block copolymer (SEPS), a styrene-isobutylene-styrene block copolymer (SIBS) and combinations thereof.

* * * * *